United States Patent [19]
Hahnen et al.

[11] Patent Number: 5,980,519
[45] Date of Patent: *Nov. 9, 1999

[54] ELECTROCAUTERY PROBE WITH VARIABLE MORPHOLOGY ELECTRODE

[75] Inventors: Kevin F. Hahnen, Miami; Gary R. Dill, Lauderhill, both of Fla.

[73] Assignee: Symbiosis Corporation, Miami, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/688,381

[22] Filed: Jul. 30, 1996

[51] Int. Cl.⁶ ................................................. A61B 17/39
[52] U.S. Cl. ............................... 606/49; 606/41; 606/47; 600/374
[58] Field of Search .......................... 606/41, 42, 45–50; 128/642; 607/100–102, 115, 116, 122; 600/372–374

[56] References Cited

U.S. PATENT DOCUMENTS

| | | |
|---|---|---|
| 4,003,380 | 1/1977 | Wien . |
| 4,054,143 | 10/1977 | Bauer . |
| 4,467,802 | 8/1984 | Maslanka . |
| 4,917,082 | 4/1990 | Grossi et al. . |
| 5,234,429 | 8/1993 | Goldhaber . |
| 5,275,615 | 1/1994 | Rose . |
| 5,282,806 | 2/1994 | Haber et al. . |
| 5,318,564 | 6/1994 | Eggers ................................ 606/47 |
| 5,354,295 | 10/1994 | Guglielmi et al. ................ 606/41 |
| 5,354,296 | 10/1994 | Turkel ................................ 606/41 |
| 5,397,342 | 3/1995 | Heil, Jr. et al. ................... 128/642 |
| 5,478,350 | 12/1995 | Kratsch et al. ................... 606/205 |
| 5,482,037 | 1/1996 | Borghi ............................... 128/642 |

FOREIGN PATENT DOCUMENTS

WO 93/20759  10/1993  WIPO .

*Primary Examiner*—Michael Peffley
*Attorney, Agent, or Firm*—Testa, Hurwitz & Thibeault, LLP

[57] ABSTRACT

An electrocautery probe with a variable morphology electrode includes a coil electrode extending through the distal end of a probe, an adjustment mechanism operable from a proximal end of the probe for changing the morphology of the coil electrode, and a connection for receiving a current for application through the electrode. The morphology of the electrode can be changed by adjusting the length of electrode which extends from the probe. In a preferred embodiment, the morphology of the electrode can also be changed through the use of slider having a shaped head which extends from the distal end of the probe and presses against the electrode. The shaped head of the slider can have a variety of shapes and when the shaped head of the slider urges against the electrode, the electrode is formed to the same shape as that of the distal end of the slider head. Also provided are mechanisms for adjusting and maintaining the position of the slider and shaped head with respect to the electrode.

20 Claims, 14 Drawing Sheets

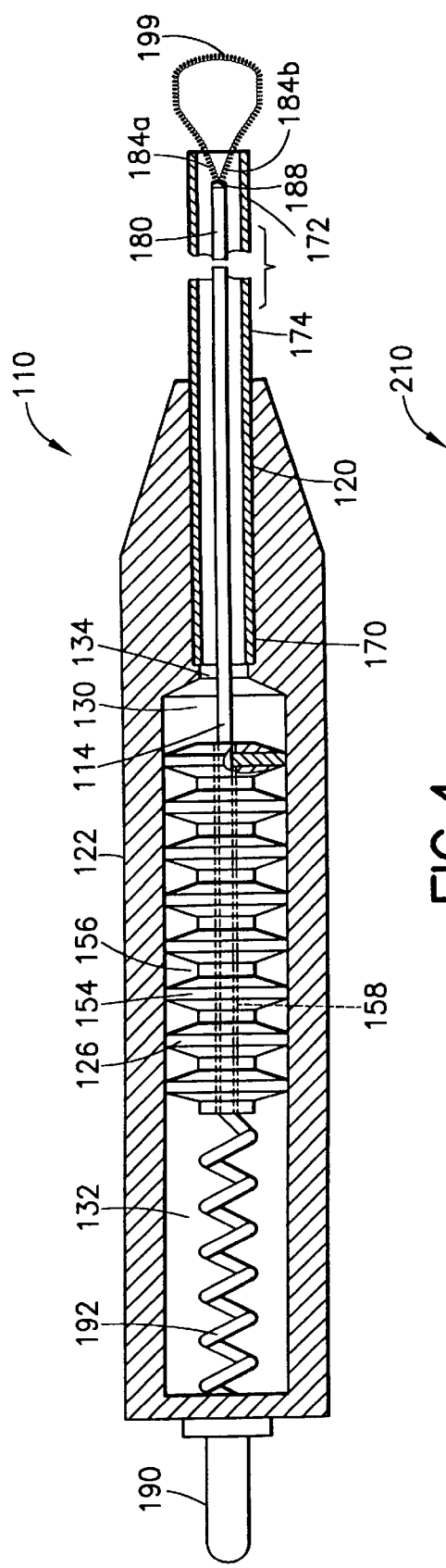
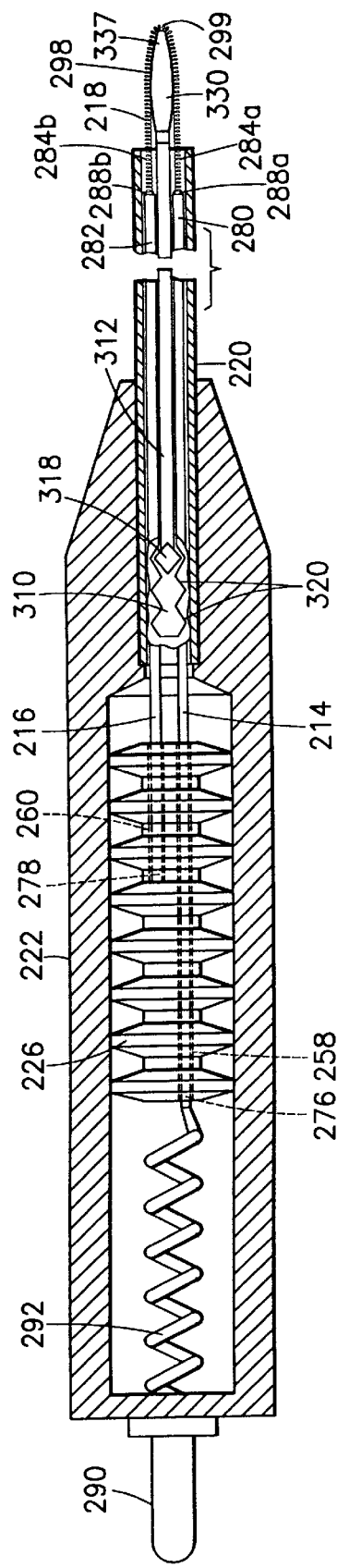
FIG. 4
FIG. 6

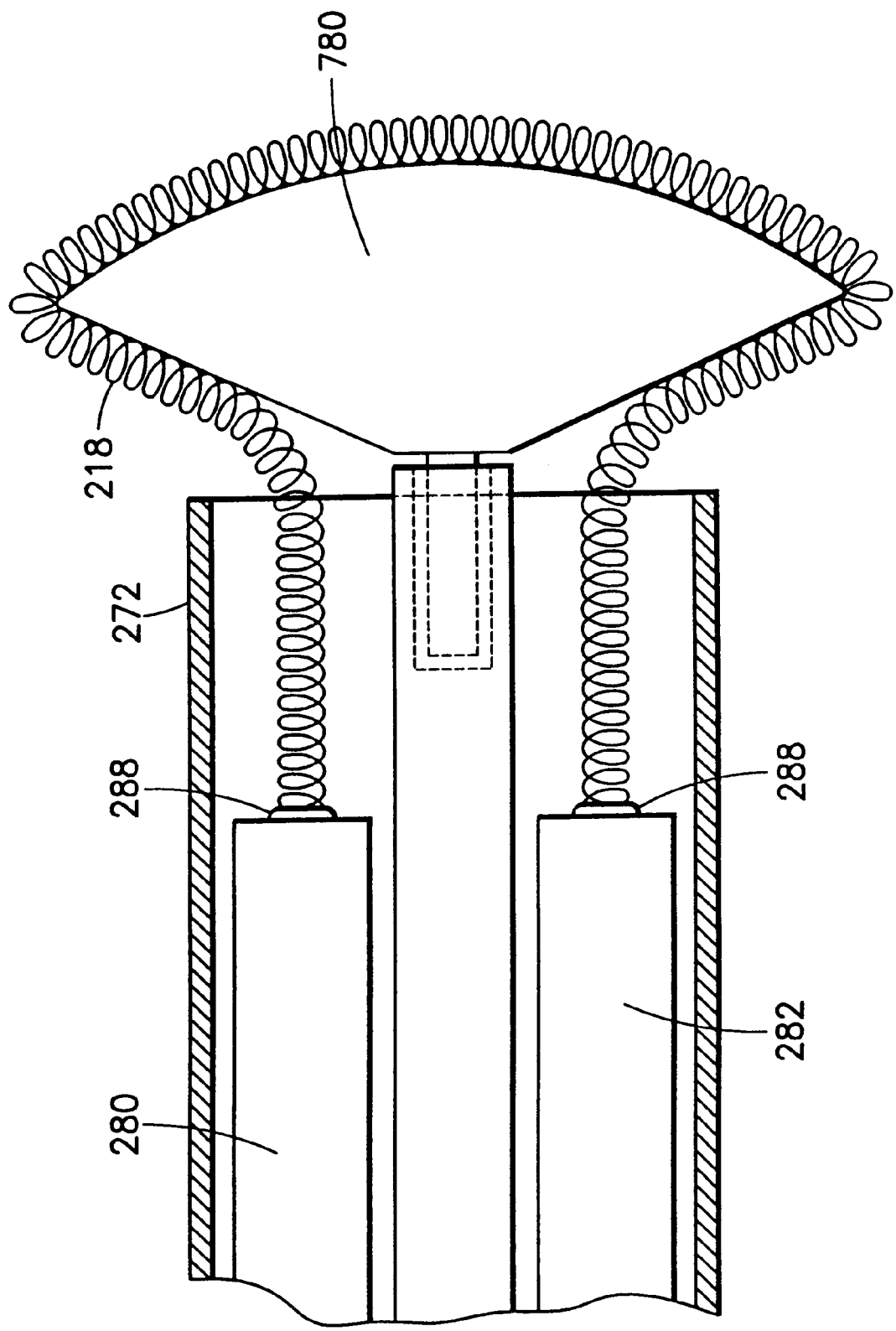

ELECTROCAUTERY PROBE WITH VARIABLE MORPHOLOGY ELECTRODE

This invention relates to co-owned U.S. Pat. No. 5,354,296, entitled "Electrocautery Probe With Variable Morphology Electrode" and co-owned U.S. Pat. No. 5,478,350, entitled "Rack and Pinion Actuation Handle For Endoscopic Instruments", which are hereby incorporated by reference herein in their entireties.

BACKGROUND OF THE INVENTION

1. Field of the Invention

This invention relates generally to medical instruments. More particularly, this invention relates to an electrocautery probe which has an electrode of adjustable shape and/or size. The invention finds particular application in endometrial ablation, prostatic ablation, and other electrocautery procedures.

2. State of the Art

Endometrial ablation is an alternative procedure to hysterectomy for women with menorrhagia (abnormal or excessive uterine bleeding). In the past, various methods of ablation, including cryosurgery and laser surgery, have been used. More recently, electrocautery techniques have also been used. Endometrial ablation by electrocautery is usually accomplished with a resectoscope and a coagulation electrode mounted on the distal end of an electrocautery probe. The resectoscope includes a telescope for viewing the interior of the uterus, a handle assembly commonly referred to as the working element, and an outer sheath. The working element is generally capable of sliding the probe with a distally mounted electrode axially through the telescope. The outer sheath is placed into the uterus prior to introducing the other elements of the resectoscope.

The actual endometrial ablation procedure involves applying a cauterizing current to the electrode and moving the electrode slowly over the entire endometrium (uterine lining) while viewing through the scope. Thermal energy is applied to the endometrial lining of the uterus by the electrode so that the endometrium is destroyed by cauterization and subsequently scars. In order to effect complete destruction of the endometrium, the electrode is moved in a systematic manner, generally beginning at the Fallopian tube ostia (mouth), proceeding to the fundus (above the uterine tubes), and continuing on the anterior, posterior, and lateral uterine walls down to the internal os of the cervix. It is well known, however, that the uterine cavity has acute corners (the cornua and tubulo-interstitial areas) as shown by reference 12 in FIG. 1 and that a relatively small electrode must be used to effectively cauterize these portions of the endometrium. Other portions of the uterus, however, are relatively broad (14 and 16 in FIG. 1) and the use of a small electrode in these areas is tedious and time consuming.

Known electrodes for use in resectoscopes are available in many different shapes and sizes. U.S. Pat. No. 4,917,082 to Grossiet al., for example, discloses several embodiments of a "Resectoscope Electrode" including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semicircular wires, hooks, spatulas and blunt tips.

Recently, the generally preferred electrode for use in endometrial ablation is the roller (often referred to as "rollerbar" or "roller ball") electrode depicted in prior art FIGS. 2a–2c. Such roller ball electrodes are available from Richard Wolf Medical Instruments Corp., Rosemont, Ill. or from Olympus Corp., Lake Success, N.Y. The roller bar 22 or roller ball 24 is approximately 2.5 mm long (e.g., 2.5 mm in diameter for the ball) and, as shown in FIGS. 2a–2c, is mounted on the distal end of an electrocautery probe 26. The distal ball or bar is supplied with a cauterizing current through conductors 28, 30 in the probe and is rolled across the endometrial surface methodically until all areas of the endometrium have been cauterized. Because of its small size, the ball or bar fits easily into the acute corners of the uterus. Its relatively small size, however, also renders it inefficient when used in the other portions of the uterus.

While it is possible to change from one electrode having a first size to another electrode having a second size during the ablation procedure, the changing of electrodes adds time to the procedure, increases the chance that the entire endometrium will not be properly ablated, and requires that a plurality of tools which are typically disposed of after use be utilized. Moreover, it has not been the general practice to change from one electrode to another during the ablation procedure. Thus, by using such a small electrode throughout the uterus, the ablation procedure takes longer and the chance of missing one or more portions of the endometrium is enhanced. Similar problems exist in other electrocautery procedures where an electrode of one shape or size is necessary for part of the procedure but is inefficient or inapplicable for another part of the procedure.

Co-owned U.S. Pat. No. 5,354,296 to Turkel discloses variable morphology electrodes, solving many of the problems associated with previous electrodes for the ablation procedure. As used herein, the term "morphology" refers to the shape and/or size of the electrode. The variable morphology electrodes vary in length and width to reach the various areas of the uterus with greater efficiency. The electrodes can be designed from volute spring portions, a plurality of cylinder elements, a springy wire mounted with beads, a plurality of loops, a band with tapering width and other shapes. However, while the disclosed electrodes of variable morphology can effectively change size, each electrode is generally limited to a specific shape which it can assume. In addition the electrodes lack the ability to have their shapes precisely controlled.

SUMMARY OF THE INVENTION

It is therefore an object of the invention to provide an electrocautery probe for use in electrocautery procedures having a flexible electrode.

It is also an object of the invention to provide an electrocautery probe having an electrode formed from a conductive coil.

It is another object of the invention to provide an electrocautery probe for use in electrocautery procedures in which the morphology of the electrode is adjustable.

It is a further object of the invention to provide an electrocautery probe having means for easily and rapidly adjusting the morphology of the electrode while the electrocautery probe extends from a resectoscope.

It is an additional object of the invention to provide an electrocautery probe with a flexible electrode having a variable surface area and where the surface area of the electrode is adjustable while the electrocautery probe extends from a resectoscope.

In accord with these objects which will be discussed in detail below, the variable morphology tool for ablation of the invention broadly includes a looped cautery coil electrode, extending from the distal end of a probe, and means for applying a cautery current or voltage across the electrode. According to a preferred aspect of the invention, adjustment means operable from a proximal end of the probe are provided for changing the morphology of the electrode. According to one embodiment, the morphology of the coiled electrode is changed by providing a means for adjusting the length of the coil which extends from the probe. Numerous other embodiments are provided which change the morphology of the electrode through the use of slider fitted with a shaped head which extends out of the distal end of the probe and presses against the electrode, conforming the electrode to a desired shape. The shaped head can take any of a variety of shapes and a shaped head most suitable for a particular procedure can be utilized. When the shaped head is moved away from the coil, the coil resumes its natural loop shape. Also provided are means for adjusting the position of the slider.

Additional objects and advantages of the invention will become apparent to those skilled in the art upon reference to the detailed description taken in conjunction with the provided figures.

BRIEF DESCRIPTION OF THE DRAWINGS

FIG. 4 is a broken top view in partial section of the embodiment of FIG. 3;

FIG. 6 is a broken top view in partial section of the embodiment of FIG. 5;

FIGS. 8a–b, 9a–b, 10a–b, and 11 are broken side elevation and top views of partial sections of an electrocautery probe kit according to the invention;

DETAILED DESCRIPTION OF THE PREFERRED EMBODIMENTS

Figure 1:
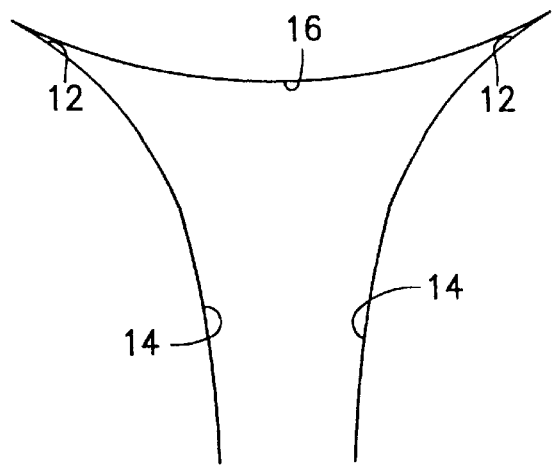
FIG. 1 is a schematic view of the uterine walls showing the acute angles and broad portions of the endometrium.
Figure 2A:
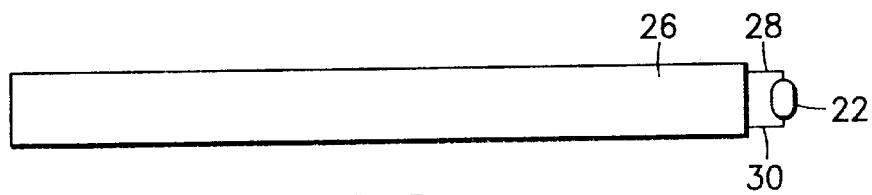
FIGS. 2a and 2b show top view schematics.
Figure 2B:
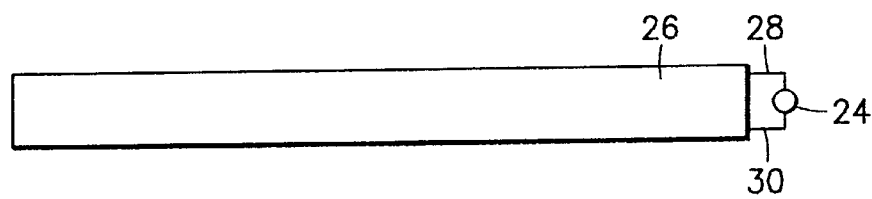
Figure 2C:
FIG. 2c shows a side view schematic of prior art roller ball and roller bar electrodes.
Figure 3:
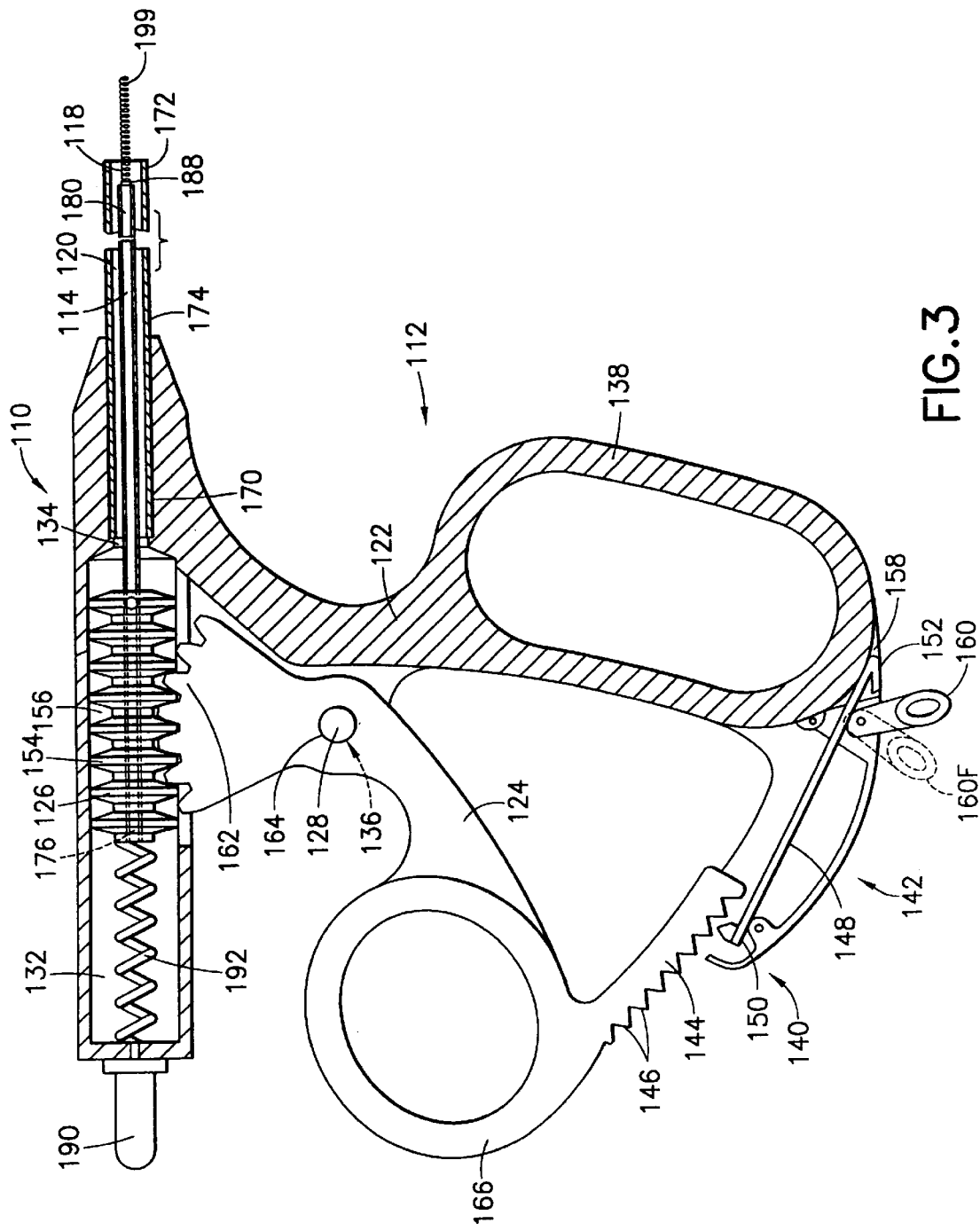
FIG. 3 is a broken side elevation view in partial section of a first embodiment of the invention.
Figure 5:
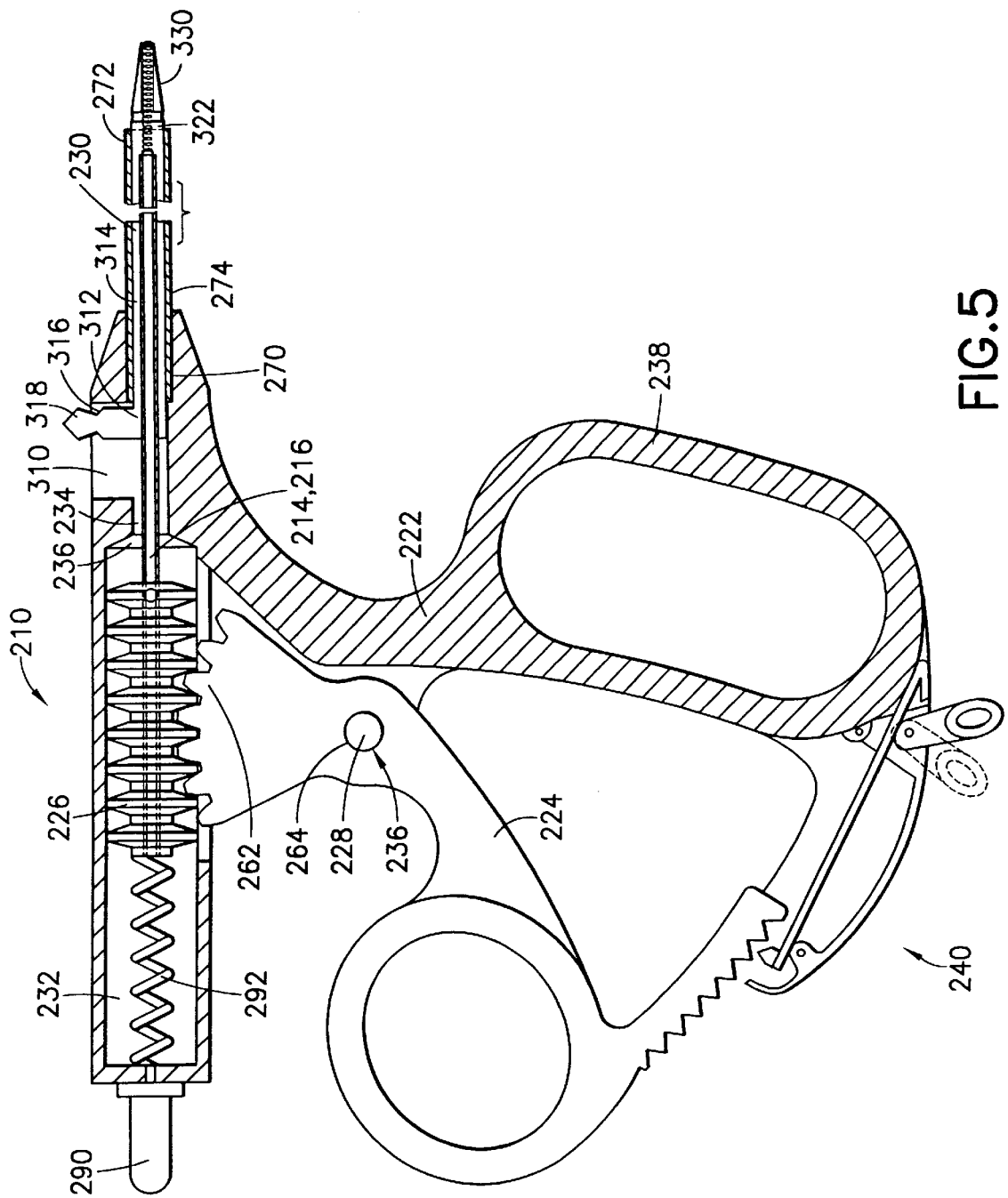
FIG. 5 is a broken side elevation view in partial section of a second embodiment of the invention.

Referring now to FIGS. 3 and 4, the electrocautery probe 110 according to the invention broadly includes a proximal adjustment handle 112, a conductive rod 114, a flexible distal electrode coil 118, and a tubular member 120. The proximal adjustment handle 112 includes a stationary member 122, a lever (or movable member) 124, and a rack member 126. The stationary member 122 has a stepped throughbore 130 having a larger proximal diameter 132 and smaller distal diameter 134, a pivot bore 136, and a lower finger ring 138 having a catch assembly 142 for a ratchet locking mechanism 140. The rack member 126 is slidably disposed within the proximal end 132 of the first throughbore 130 and includes alternating cogs 154 and grooves 156 and an axial throughbore 158 for receiving the rod 114. The lever 124 has an upper pinion portion 162 for engaging the cogs 154 and grooves 156 of the rack member 126, a pivot bore 164, and a lower thumb ring 166 having a ratchet 144 for the ratchet locking mechanism 140. The lever 124 is pivotally coupled to the stationary member by a pin 128 placed through the pivot bores 136, 164. The actuation handle is described fully in co-owned U.S. Pat. No. 5,478, 350.

The tubular member 120 has a proximal end 170 and a distal end 172. The proximal end 170 of the tubular member 120 is engaged in the distal end 134 of the first throughbore 130. The tubular member is covered in a non-conductive material 174, such as an FEP sheath. The proximal end 176 of the rod 114 is received within the throughbore 158 of the rack member 126 and extends out the proximal end of the rack member. The distal end 180 of the rod 114 extends through the tubular member and, near the distal end 172 of the tubular member 120, is coupled by a weld 188 to the two ends 184a, 184b of the flexible electrode coil 118. By coupling both ends 184a, 184b of the electrode coil 118 to the distal end 180 of the rod 114, a loop of electrode coil is formed. The loop of electrode coil exits the distal end 172 of the tubular member 120 and forms the exposed electrode portion 199 of the probe. It will be appreciated that by pivoting the lever 124 with respect to the stationary member 122, the exposed electrode portion 199 of the probe is adjusted.

The coil electrode is made from a high temperature spring material. Preferably the material is one of nichrome, titanium, or nickel- or cobalt-superalloy. Stainless steel may also be used, but may not be suitable at high power levels, due to the temperatures achieved at the coil.

At the proximal end of the stationary member 122, a clip 190 is provided for coupling to a cautery voltage means (not shown). A spring-like conducting wire 192 is provided proximal of the rack member 126 within the first throughbore 130 of the stationary member. The proximal end of the wire 192 is coupled to the clip 190 (preferably by soldering) and the distal end of the wire is coupled, also preferably by soldering, to the proximal end 176 of the rod 114. The spring-like wire is permits a connection to be maintained between the voltage means and the rod 114 even as the rack member 126 is moved axially within the first throughbore 130. When a voltage is applied to the clip 190, it will be appreciated that current travels through the spring-like conducting wire to the rod and out the loop of the coil.

The ratchet element 144 of the ratchet locking mechanism 140 extends from the lower thumb ring 166 of the lever 124. The lower finger ring 138 of the stationary member 122 includes the catch assembly 142 for the ratchet locking mechanism 140. The ratchet element 144 has a plurality of teeth 146 radially displaced from the pivot pin 128. The catch assembly 142 further includes a cantilevered resilient strip 148 having at one end a locking barb 150 facing the teeth 146 of the ratchet element 144 and at the other end a downward bent barb 152 locked into a slot 158 for securing the cantilevered strip in the stationary member 122. A cam lever 160 in a first position forces the locking barb 150 to engage a tooth 146 of the ratchet element 144, locking the lever 124 relative to the stationary member 122, and in a second position releases the barb allowing the lever to pivot freely relative to the stationary member. The ratchet locking mechanism 140 enables the lever and the stationary member to be locked into a number of positions, enabling the electrode 199 to temporarily be maintained at one size, and then adjusted to another, according to the requirements of the ablation procedure. The ratchet locking mechanism is described fully in previously incorporated U.S. Pat. No. 5,354,296.

Turning now to FIGS. 5, 6 and 7a–b, in a second embodiment, generally similar to the first embodiment (with numbers incremented by 100 referring to like parts of the first embodiment), an electrocautery probe 210 includes two rods 214, 216, a flexible electrode coil 218, a tubular member 220, a stationary member 222, a lever 224, a rack member 226, and a pivot pin 228. The stationary member 222 has a stepped throughbore 230 having a larger proximal diameter 232 and smaller distal diameter 234, and a lower finger ring 238 having a catch assembly 242 for the ratchet locking mechanism 240. The rack member 226, slidably disposed within the proximal end 232 of the throughbore 230 of the stationary member, includes two parallel throughbores 258, 260 for receiving the rods 214, 216. The lever 224 has an upper pinion portion 262 for engaging the rack member 226 and is pivotally coupled to the stationary member 222 by a pivot pin 228.

The tubular member 220 has a proximal end 270 engaged in the distal end 234 of the throughbore 230 of the stationary member 222 and a distal end 272. The tubular member is covered in a non-conductive material 274, such as an FEP sheath. The proximal ends 276, 278 of the rods 214, 216 are received within the throughbores 258, 260 of the rack member 226, with one of the rods 214 extending all the way through one of the throughbores 258. The distal ends 280, 282 of the rods 214, 216 extend through the tubular member and, near the distal end 272 of the tubular member 220, are coupled to the two ends 284a, 284b of the coil 218 by a weld 288a, 288b. By coupling both ends 284a, 284b of the coil 218 to the distal ends 280, 282 of the rods 214, 216 a U-shaped loop of the coil electrode 218 is formed. The loop exits the distal end 272 of the tubular member 220 and forms the exposed portion of the electrode 299 of the probe 210. One of the rods 214 is coupled to a cautery clip 290 by a spring-like wire 292 which is soldered to both the rod and the clip.

A longitudinal notched cutout 310 is provided in the stationary member 222 and intersects the distal end 234 of the throughbore 230 of the stationary member. A longitudinal slider 312 having radially extending knob 318 is slidably disposed between the rods 214, 216 and extends through the tubular member 220 to the distal end 272 of the tubular member. The knob 318 of the slider 312 extends radially out of the notched cutout 310. The knob is preferably diamond-shaped in cross-section at the location of the cutout. The notched cutout 310 is shaped with a plurality of resilient stops 320 through which the diamond-shaped knob 318 can be forced distally and proximally. With this arrangement, the knob 318 can be forced from one resilient stop to another and the slider 312 moved into a number of defined positions axially within the tubular member such that the distal end 322 of the slider will withdraw into or extend from the distal end 272 of the tubular member 220. The distal end 322 of the slider 312 includes a receiving hole 324.

Figure 7A:
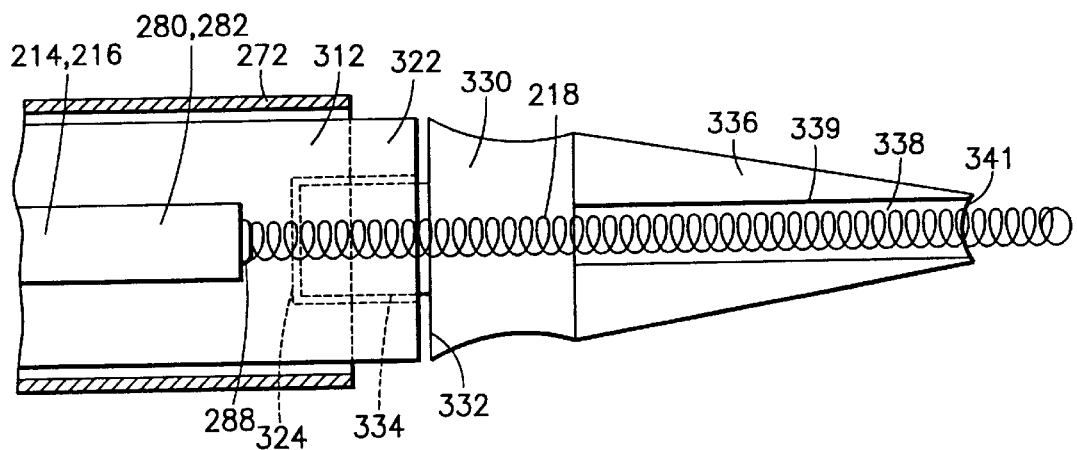
FIGS. 7a and 7b are broken side elevation views of the distal end of the second embodiment of FIG. 5.
Figure 7B:
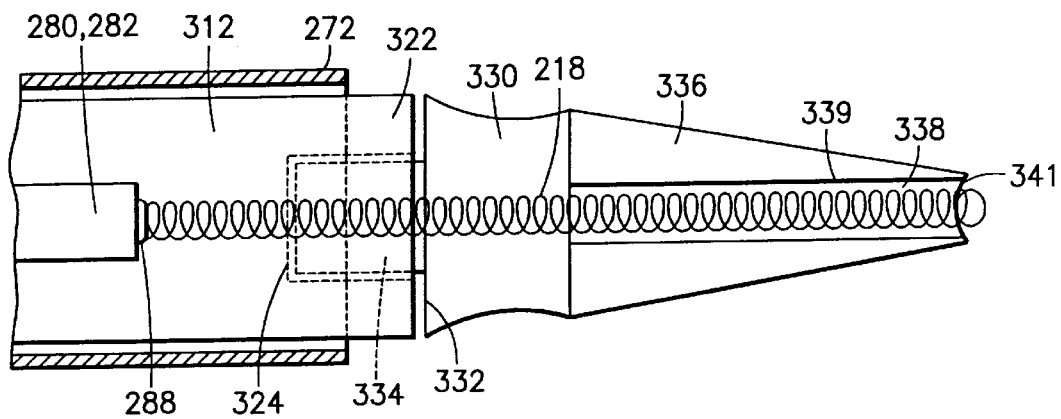

Referring to FIGS. 7a and 7b, a shaped head 330, preferably sized to fit within the lumen for the tubular member, includes a proximal protrusion 334 and a tapered distal end 336. The protrusion 334 is press fit or snap fit into the receiving hole 324. The tapered distal end 336 of the shape head 330 is sized so that it will move in and out of the distal end 272 of the tubular member 220 without resistance. The vertical dimension of the shaped head narrows from the proximal end 332, where it has approximately the same vertical dimension as that of the slider 312, to the distal end 336, where it has approximately the same vertical dimension as that of the diameter of the coil electrode 218. A channel 338 is provided around the perimeter of the tapered distal end of the shaped head for engaging the coil 218 so that the coil does not slip off the shaped head. The channel 338 is deeper along the sides 339 of the shaped head 330 than along the distal end 341, so as to accommodate the full diameter of the coil at the sides 339 and permit the coil to move freely in and out of the distal end 272 of the tubular member 220 even when the shape head 330 is withdrawn into the tubular member 220. It will be appreciated that as the rods 214, 216 are moved to their most distal position, the largest length of coil 218 extends from the distal end 272 of the tubular member 220, thereby allowing easier placement of the shaped head 330 within the loop of the coil and easier insertion of the shaped head into the receiving hole 324 (FIG. 7a). When the shaped head extends out of the distal end of the tubular member 220 and the rods 214, 216 are moved proximally, the coil electrode 218 tightens around and conforms to the shape of the shaped head 330 (FIG. 7b).

Figure 8A:
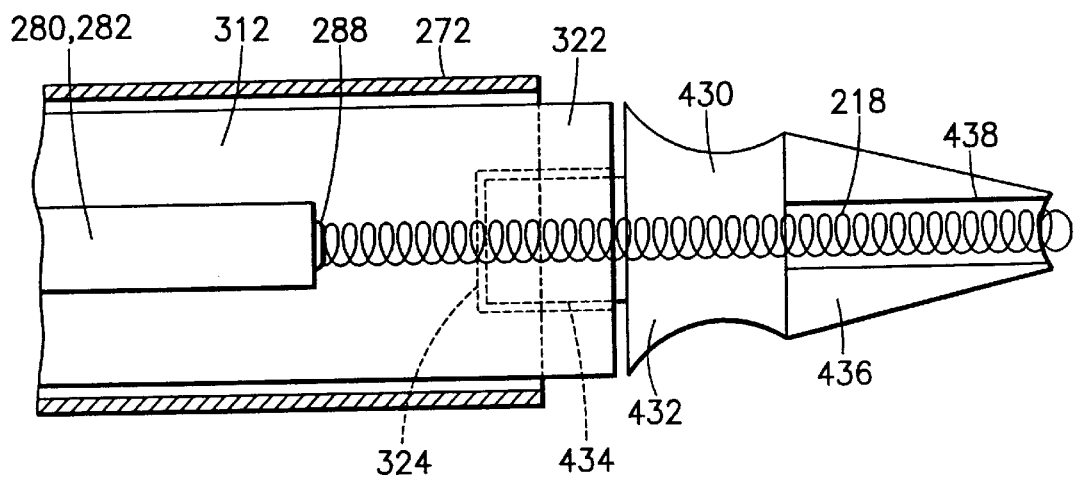
Figure 8B:
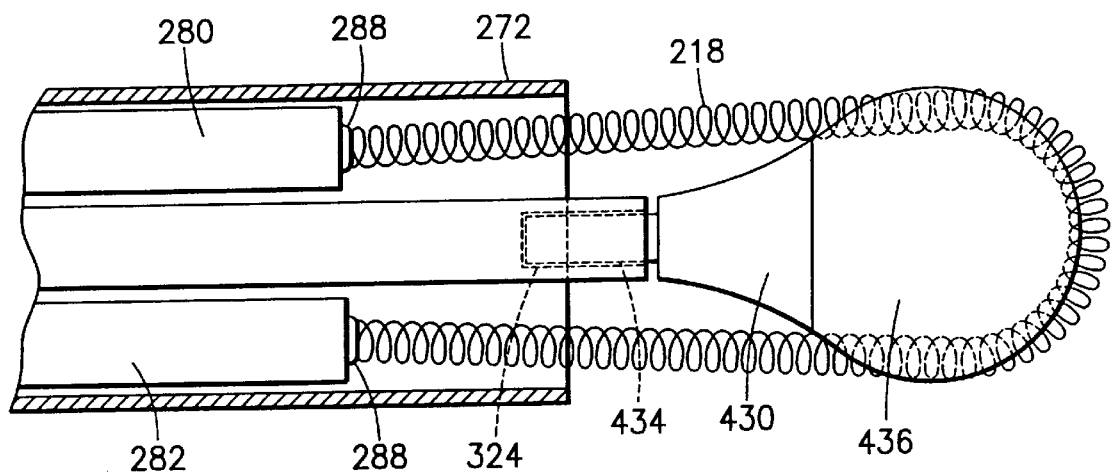
Figure 9A:
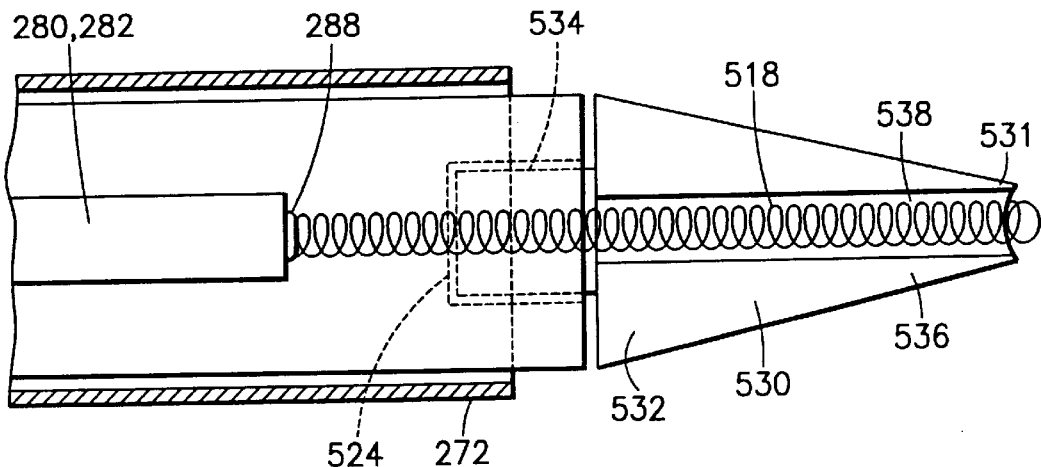
Figure 9B:
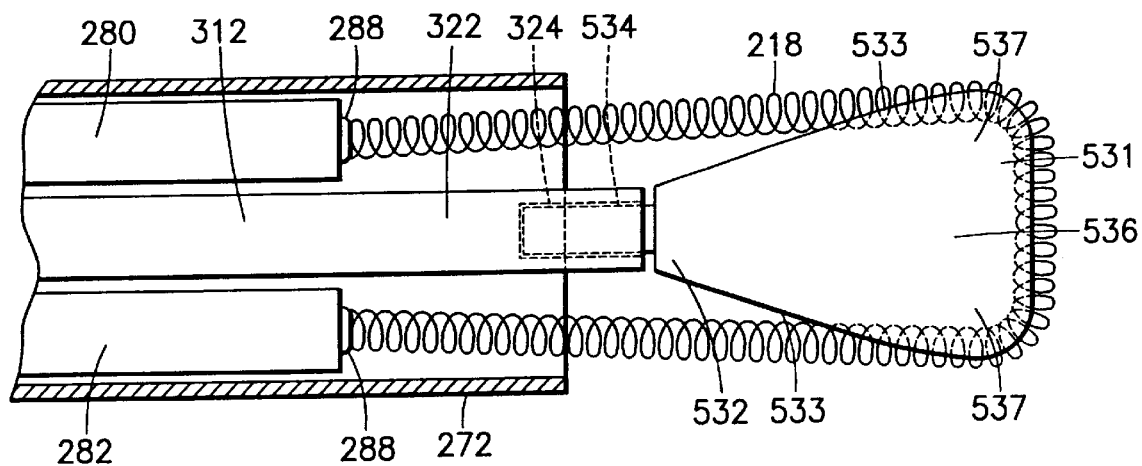
Figure 10A:
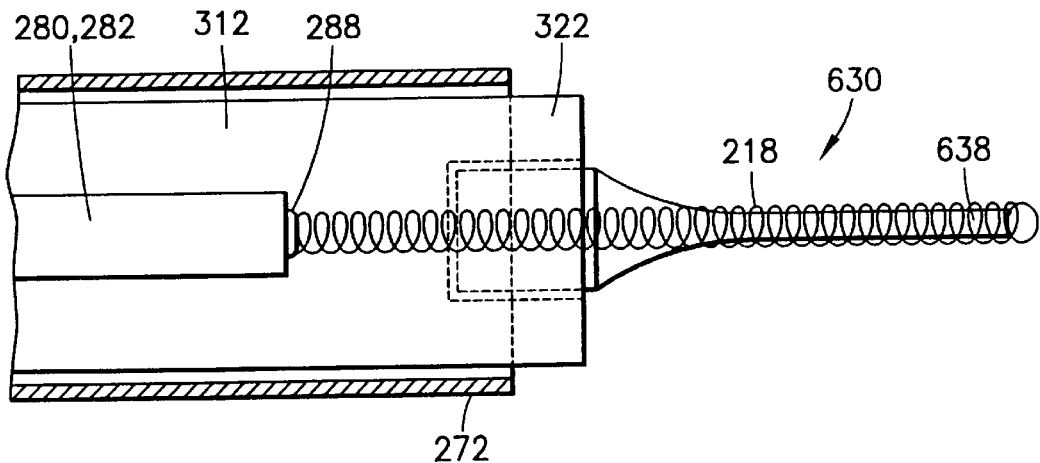
Figure 10B:
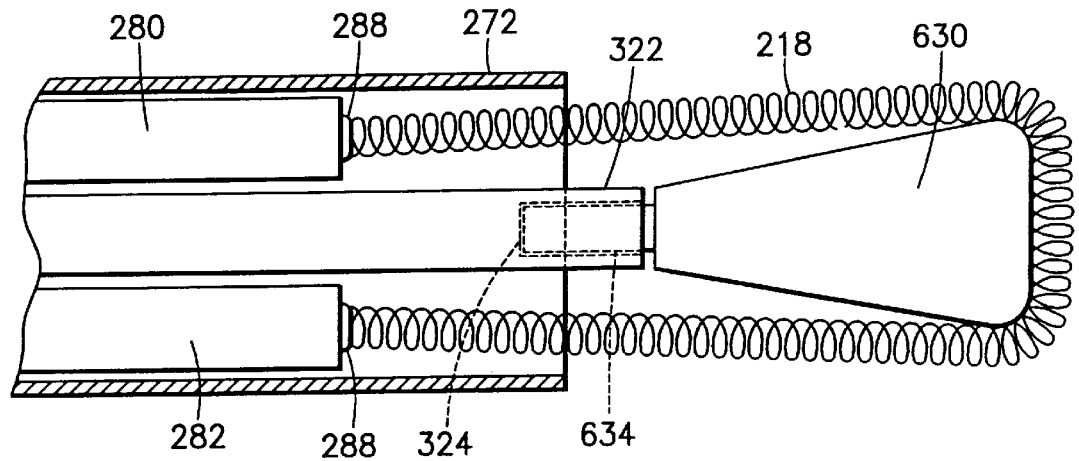

Referring to FIGS. 8a, 8b, 9a, 9b, 10a, 10b and 11, in a preferred aspect of the invention an electrocautery probe kit is provided with a plurality of shaped heads which are removably coupled to the slider 312. A first shaped head 430 has a substantially circular-shape and includes a proximal end 432 and a distal portion 436 (FIGS. 8a and 8b). The distal portion 436 includes a circumferential channel 438 for receiving and engaging a portion of the coil 218. The shaped head 430 tapers from the proximal end 432, where it has a vertical dimension approximately the same as that of the distal end 322 of the slider 312, to the distal portion, where it has a vertical dimension approximately that of the diameter of the coil 218. A protrusion 434, substantially the same size as the receiving hole 324 of the slider 312, is included at the proximal end 432 and frictionally engages the receiving hole. A second shaped head 530 has a generally triangular-shape (FIGS. 9a and 9b). The second shaped head 530 includes a base side 531 at a distal end 536, two sides 533 which angle outward toward the distal end 536, and a shallow channel 538 along the base side 531 and along the rounded corners 537. The channel is deeper along the rounded corners 537 to permit the coil to move freely in and out of the tubular member even when the shaped head 530 is withdrawn into the distal end 272 of the tubular member. The vertical dimension of the shaped head 530 decreases from its proximal end 532 to its distal end 536. A third shaped head 630 has a thin elongate shape (FIGS. 10a and 10b). The shaped head 630 is provided with a side channel 638 having a constant and narrow depth. The depth for the channel is narrower than the coil 618. As a result of the thin shape of the head, the narrow channels, and the constant shallow depth of the channels, cautery is permitted on the top and bottom of the coil and along the sides of the coil as the coil is dragged over tissue. In addition, the shaped head 630 can easily be maneuvered into narrow areas. A fourth shaped head 730 is provided which has a distal end wider than the diameter of the distal end of the tubular member 272

(FIG. 11). The shaped head 730 enables an electrode to have a greater surface area than one shaped by a shaped head withdrawable into the tubular member.

Figure 12:
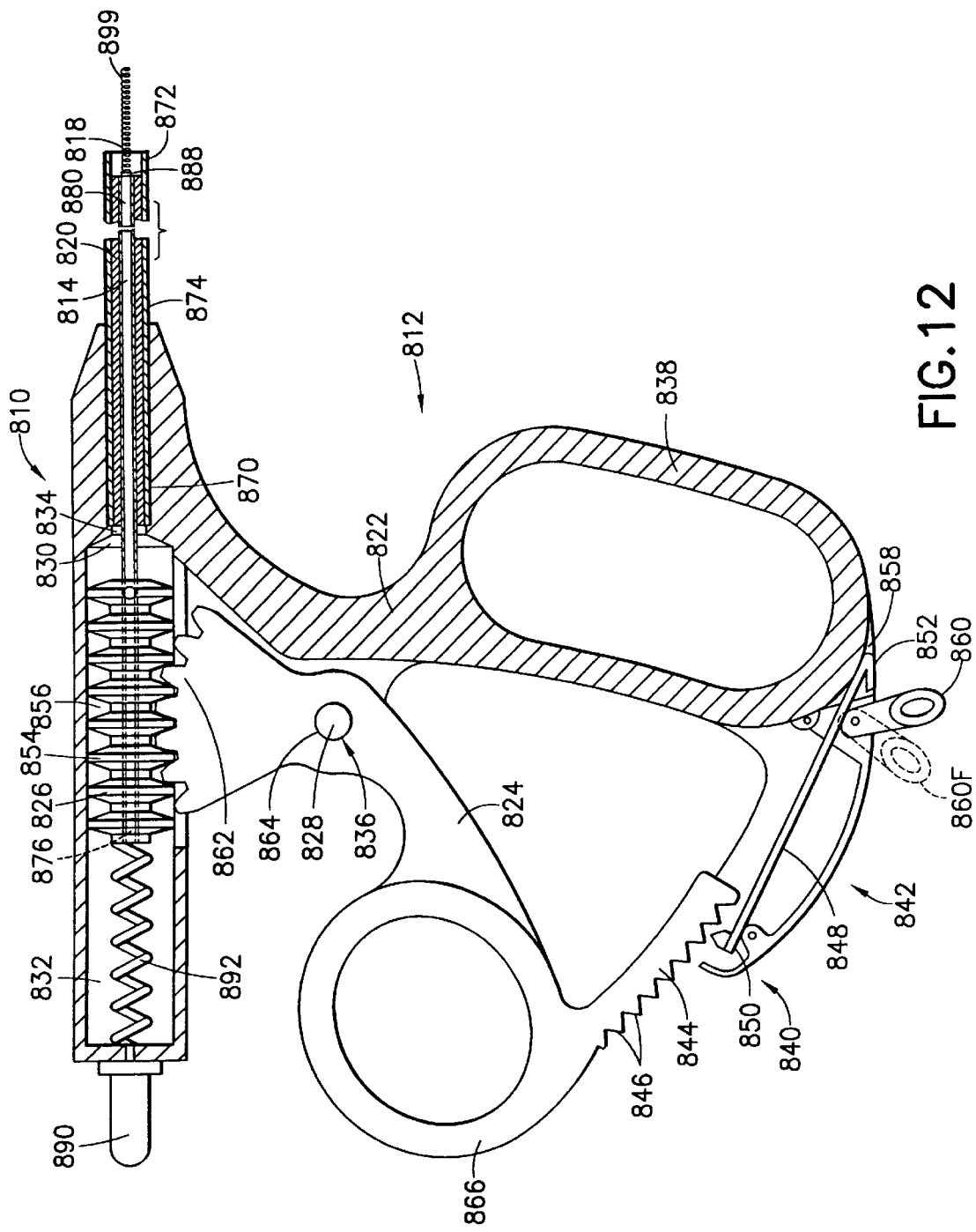
FIG. 12 is a broken side elevation view in partial section of a third embodiment of the invention.
Figure 13:
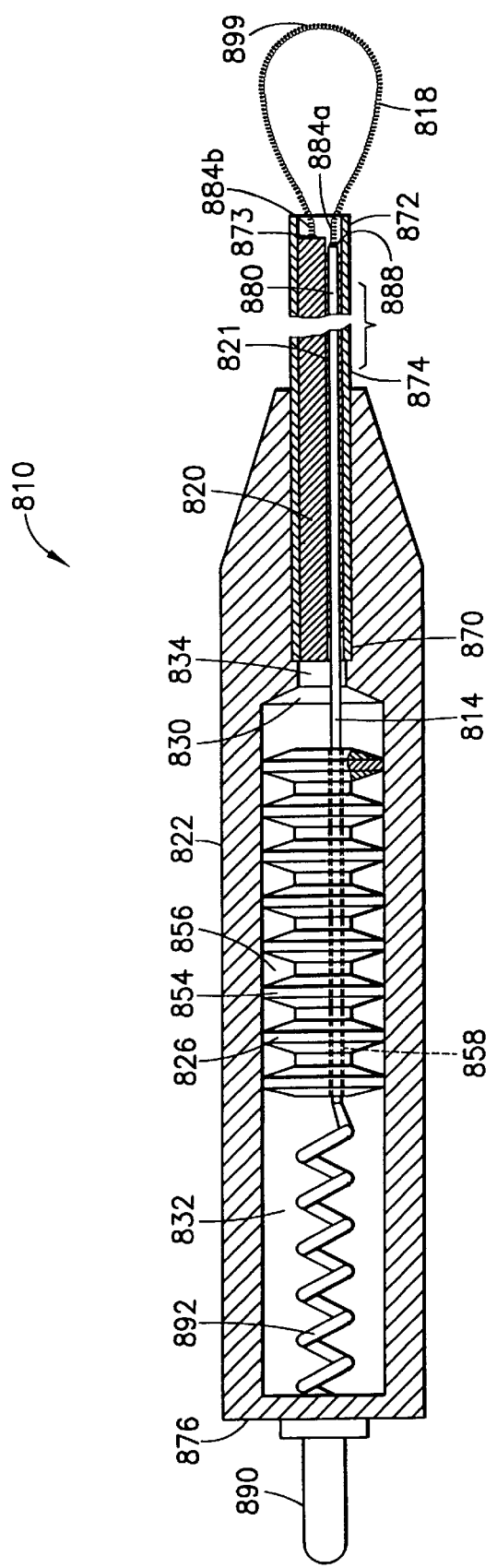
FIG. 13 is a broken top view in partial section of the embodiment of FIG. 12.

Turning to FIGS. 12 and 13, a third embodiment of the invention, substantially similar to the first embodiment (with numbers incremented by 700 referring to like parts of the first embodiment), is shown. An electrocautery probe 810 includes a rod 814, a conductive coil 818, a cylindrical member 820, a stationary member 822, a lever 824, a rack member 826, and a ratchet locking mechanism 840. The proximal adjustment handle 812 operates as previously disclosed herein with reference to the second embodiment and with reference to previously incorporated U.S. Pat. No. 5,478,350. The ratchet locking mechanism also operates as previously disclosed herein and with reference to previously incorporated U.S. Pat. 5,354,296.

The rack member 826 includes a non-axial throughbore 858 for receiving a conductive rod 814. The cylindrical member 820 includes a non-axial lumen 821 having a distal end 872, a proximal end 870, and a shallow distal bore 873 parallel to the non-axial lumen 821. The proximal end 870 of the cylindrical member 820 is engaged in the distal end 834 of the throughbore 830 of the stationary member 822 and the non-axial lumen 821 is aligned with the throughbore 858 of the rack member 826. The cylindrical member 820 is covered in a non-conductive material 874, such as an FEP sheath. The proximal end 876 of the rod 814 is received within the throughbore 858 of the rack member 826. The distal end 880 of the rod 814 extends through the lumen 821 in the cylindrical member 820 and near the distal end of the cylindrical member is coupled 888 to the first end 884a of the coil by a weld. The coil 818 exits the distal end 872 of the cylindrical member 820 and the second end 884b of the coil is fixed in the shallow distal bore 873 of the cylindrical member 820. It will be appreciated that by pivoting the lever 822 with respect to the stationary member 822, the rod 814 is moved axially within the lumen 821 and the length of the coil which exits from the distal end 872 of the lumen is varied. A cautery clip 890 is coupled to the proximal end 876 of the stationary member 822. The clip 890 is coupled to the proximal end 876 of the rod by a spring-like wire 892.

Figure 14:
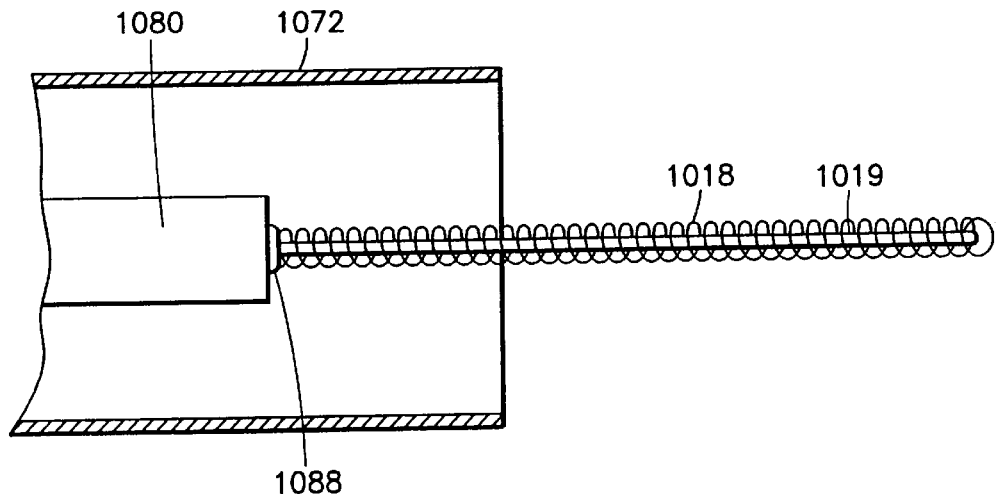
FIG. 14 is a broken side elevation in partial section of a fourth embodiment of the invention.
Figure 15:
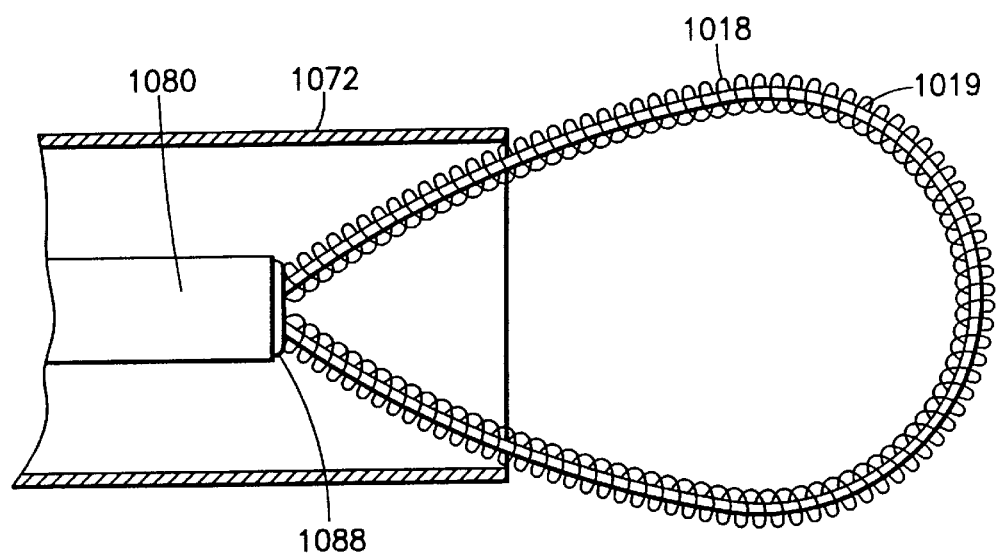
FIG. 15 is a broken top view in partial section of the embodiment of FIG. 14.

Turning now to FIGS. 14 and 15, in a fourth embodiment, generally similar to the first embodiment (with numbers incremented by 900 referring to like parts of the first embodiment), an electrocautery probe includes a coil electrode 1018 with a probe core 1019 of a resilient material extending through the coil 1018. The probe core 1019 is preferably made of a high temperature spring material, such as nitinol, nichrome, titanium, or nickel- or cobalt-superalloy. Both the probe core 1019 and the coil 1018 are coupled by a weld 1088 to the distal end 1080 of a conducting rod 1014 which moves in and out of the tube 1072. In this manner, the coil electrode 1018 can be made to assume desired configurations.

Figure 16:
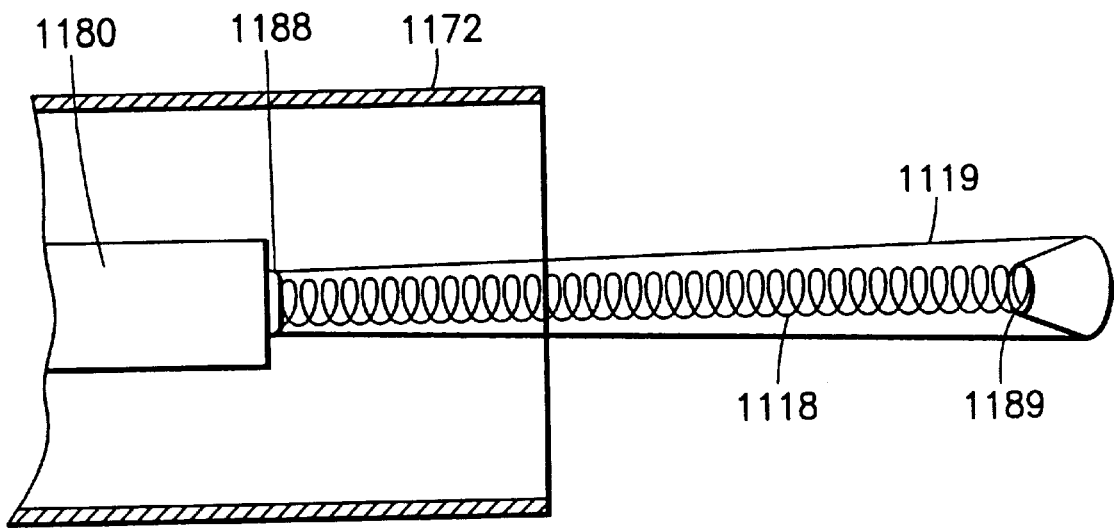
FIG. 16 is a broken side elevation in partial section of a fifth embodiment of the invention.
Figure 17:
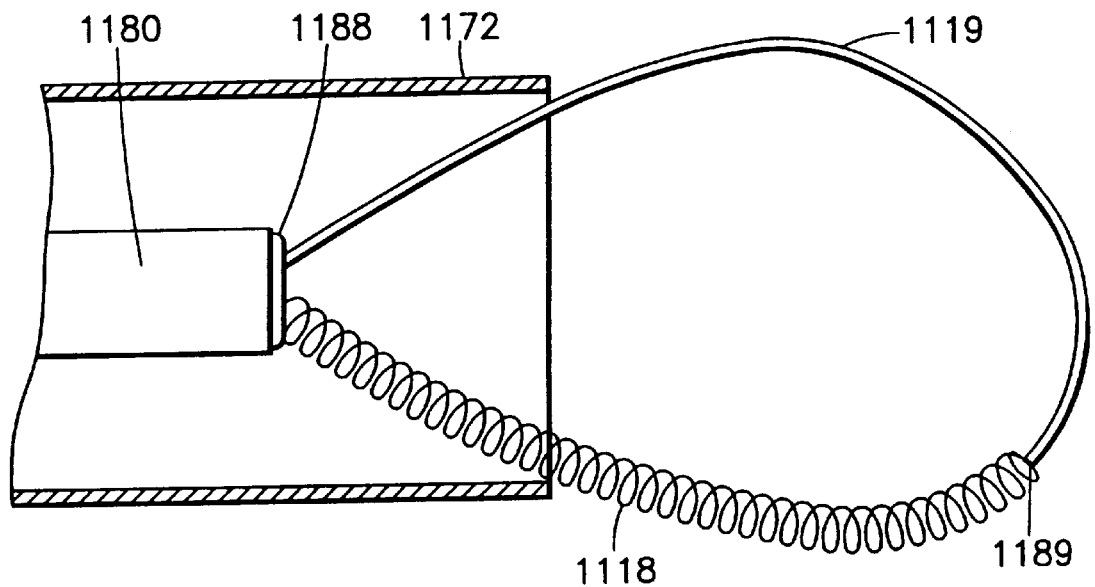
FIG. 17 is a broken top view in partial section of the embodiment of FIG. 16.

Referring to FIGS. 16 and 17, a fifth embodiment of the invention is shown, generally similar to the first embodiment (with numbers incremented by 1000 referring to like parts of the first embodiment). An electrocautery probe includes an electrode having both a coil portion 1118 and a solid portion 1119. The solid portion 1119 may be in the form of flattened stock (shown), wire, or cable and is preferably made of a high temperature spring material, such as nitinol, nichrome, titanium, or nickel- or cobalt-superalloy. The coil portion 1118 and solid portion 1119 are coupled by a weld 1188 to the distal end 1180 of a conducting rod and are coupled by a weld 1189 to each other.

Figure 18:
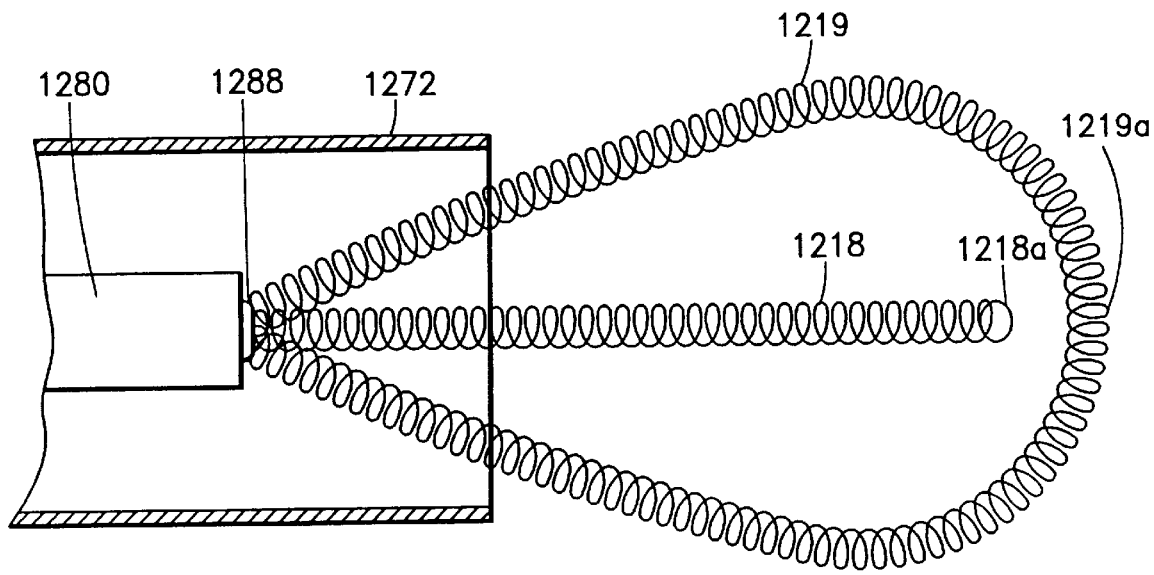
FIG. 18 is a broken side elevation in partial section of a sixth embodiment of the invention.
Figure 19:
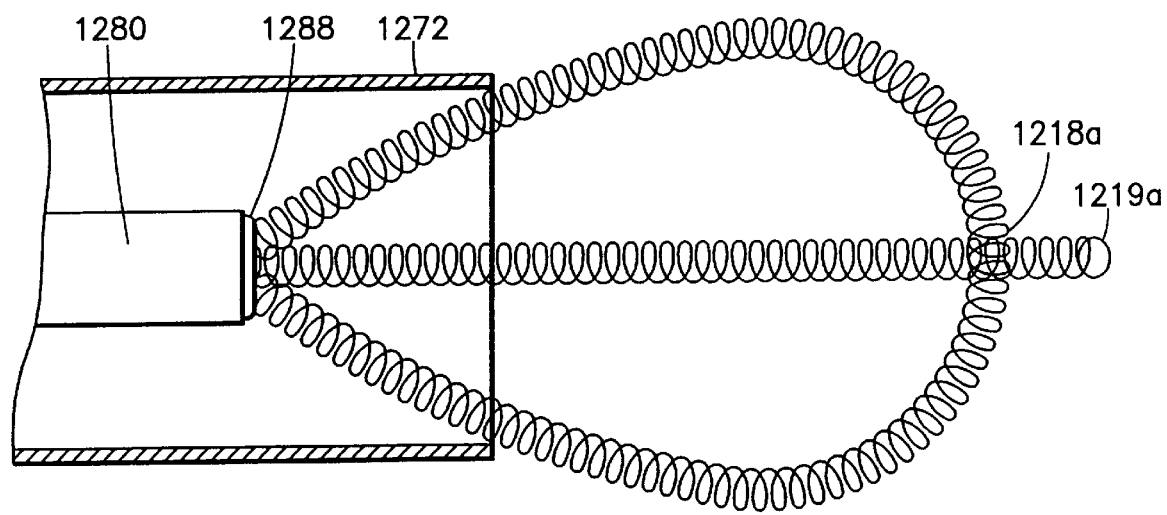
FIG. 19 is a broken top view in partial section of the embodiment of FIG. 18.

Turning to FIGS. 18 and 19, a sixth embodiment of the invention, generally similar to the first embodiment (with numbers incremented by 1100 referring to like parts of the first embodiment), is shown in which an electrocautery probe includes two looped coil electrodes 1218, 1219 coupled to and extending from the distal end 1280 of the rod. The loop of one coil electrode is offset by 90° from the other coil electrode. The electrodes are coupled by a weld 1288 to the distal end 1280 of a conducting rod. FIGS. 18 and 19 show the loop of one electrode 1218 nested within the bounds of the loop of the other electrode 1219. It will be appreciated that alternatively, both electrodes may extend the same length from the conducting rod 1280 and the coil electrodes 1218, 1219 may be intertwined at their distalmost portion 1218a, 1219a. Likewise, it will be appreciated that additional electrodes may also be coupled to the conducting rod and arranged relative to the two electrodes to provide increased surface area for cautery ablation.

There have been described and illustrated herein several embodiments of an electrocautery probe having a variable morphology electrode. While particular embodiments of the invention have been described, it is not intended that the invention be limited thereto, as it is intended that the invention be as broad in scope as the art will allow and that the specification be read likewise. Thus, while the various embodiments of the invention have been shown to include a rack and pinion handle mechanism for actuating the adjustment of the morphology of the electrode, it will be appreciated that other actuating means can also be used. For example, co-owned U.S. Patent No. 5,354,296, hereby incorporated herein, discloses an alternate handle for adjusting a variable morphology electrode. Furthermore, while the handles have each been shown with a ratchet locking mechanism to lock the handles and hence the coil in fixed positions, it will be understood that an alternative locking mechanism or no locking mechanism can be used. Also, while one embodiment is shown to include more than one electrode, it will be appreciated that other of the embodiments may also be configured to include more than one electrode. In addition, while the various embodiments disclosed herein have been shown to include a combination of either one or two movable rods, one or more electrodes (with or without a core), and in some cases a slider and shaped head, it will be recognized that the disclosure covers any combination of those. Moreover, while the electrocautery probe has been shown with one tubular member, it will be understood that two tubular or cylindrical members can be used to house the coil(s). Also, while the embodiments of the invention have been shown with a rod with the electrode which moves in and out of a tube, it will be appreciated that the rod could be stationary, and the tube could be moved back and forth over the rod and electrode (as may be seen with reference to copending co-owned U.S. Ser. No. 08/189, 937 which is hereby incorporated by reference herein in its entirety) to accomplish similar results.

Furthermore, while a slider has been shown to have a diamond-shaped knob, it will be appreciated that the slider can have an alternate shape and that the head can be otherwise shaped and/or configured so as to include other mechanisms for locking and unlocking the slider. In addition, while a notched slot with resilient stops has been disclosed for temporarily maintaining the slider in a position, it will be understood that another manner of locking and unlocking the slider can be similarly used. For example, the head of the slider can be fit with a spring-loaded push button which would enable the slider to lock into a catch when the push button is up and slide into another position when the push button is pressed in. Moreover, while particular shapes have been disclosed in reference to the shaped heads it will be appreciated that other shapes can be used as well. In addition, while a channel on the shaped head has been shown to engage the coil and secure the coil in place, it is not necessary to have a channel. Furthermore, while the shaped heads have been shown to be coupled to the slider by a protrusion fit into a receiving hole, it will be appreciated that other means for coupling the shaped head to the slider can be used. In fact, the shaped head and slider can be provided as one integral unit, and, if desired, the slider can be made sufficiently flexible so that it can be inserted via the handle through the tubular member. In this manner, different heads can be inserted into and removed from the flexible morphology electrode instrument during a single procedure without withdrawing the instrument from its location.

It will also be appreciated that while the conducting rod(s) has been disclosed in certain embodiments to extend through the second throughbore of the rack member, the rod(s) may also only partially enter the throughbore, with other conducting means further employed. In addition while the conducting rod(s) has been shown to extend through the tubular member or cylindrical member to near the distal end of the tubular member or cylindrical member, it will be understood that the conducting rod(s) need not enter the proximal end of the tubular member, and that a longer coil extending from the conducting rod(s) will suffice. Furthermore, while the coil has been shown to be welded to the distal end of the conducting rod(s), other coupling means can be used, such as soldering or crimping. Also, while a spring-like wire has been shown to be soldered to the proximal end of the conducting rod, other coupling means can be used, such as welding or crimping. Moreover, while conducting rods have been shown as a conductive means between the loop of coil electrode(s) and the cautery clip, other conducting means can be used. For example, one or more extended coil electrodes can be used such that the ends of the electrode extend through the rack and are coupled to the cautery clip. In addition, while a clip has been shown as a convenient means for connecting the variable morphology tool to a cautery voltage means, it will be appreciated that other means for coupling the tool to a cautery voltage means can be used. It will therefore be appreciated by those skilled in the art that yet other modifications could be made to the provided invention without deviating from its spirit and scope as so claimed.

We claim:

1. An electrocautery probe having a variable morphology cautery electrode for performincg cautery procedures, comprising:
    a) a tubular member having a proximal end and a distal end;
    b) at least one flexible coil cautery electrode capable of carrying a cautery current and extending at least partially out said distal end of said tubular member, each of said at least one cautery electrode having two ends, wherein at least one of said two ends is disposed within said tubular member;
    c) adjustment means coupled to said tubular member and said at least one cautery electrode for moving one of (i) said at least one of said two ends and (ii) said tubular member, relative to the other; and
    d) coupling means for coupling said at least one cautery electrode to a cautery voltage supply, wherein said adjustment means for moving, when actuated, changes the morphology of said at least one cautery electrode.

2. An electrocautery probe according to claim 1, wherein:
    said two ends of said at least one cautery electrode are coupled to said adjustment means and said at least one cautery electrode extends through said distal end of said tubular member.

3. An electrocautery probe according to claim 1, wherein:
    said adjustment means include a stationary member, and a movable member movably coupled to said stationary member, wherein movement of said movable member relative to said stationary member imparts relative movement of said at least one coil cautery electrode to said tubular member.

4. An electrocautery probe according to claim 3, wherein:
    said adjustment means further includes a rack member having a plurality of cogs and a plurality of grooves, and said stationary member includes a throughbore and said movable member includes an upper pinion portion which enters said throughbore,
    wherein said rack member is slidably disposed in said throughbore and said plurality of cogs and said plurality of grooves are engaged by said upper pinion portion, and said rack member is coupled to at least one of said two ends of said at least one coil cautery electrode, such that movement of said movable member relative to said stationary member moves said rack member axially within said throughbore and thereby moves said at least one coil cautery electrode relative to said tubular member.

5. An electrocautery probe according to claim 3, wherein:
    said adjustment means includes at least one substantially rigid rod coupling said at least one coil cautery electrode to said movable member.

6. An electrocautery probe according to claim 3, wherein:
    at least one of said movable member and said stationary member includes locking means for releasably locking said movable member relative to said stationary member.

7. An electrocautery probe according to claim 1, wherein:
    one of said two ends of each of said at least one coil cautery electrode is fixed relative to said tubular member.

8. An electrocautery probe according to claim 1, wherein:
    said adjustment means includes means for moving said two ends of each of said at least one coil cautery electrode relative to said tubular member.

9. An electrocautery probe according to claim 1, further comprising:
    e) shaping means for engaging said at least one cautery electrode and thereby changing the morphology of said at least one cautery electrode.

10. An electrocautery probe according to claim 9, further comprising:
    means for moving said shaping means relative to said at least one cautery electrode.

11. An electrocautery probe according to claim 10, wherein:
    said means for moving said shaping means moves said shaping means relative to said tubular member.

12. An electrocautery probe according to claim 11, wherein:
    said shaping means includes locking means for temporarily maintaining said shaping means in any one of a number of positions relative to said tubular member.

13. An electrocautery probe according to claim 9, wherein:
said shaping means includes a channel for engaging said coil cautery electrode.

14. An electrocautery probe according to claim 1, wherein:
said at least one coil cautery electrode is made of one of nichrome, titanium, nickel-superalloy, cobalt-superalloy, and stainless steel.

15. An electrocautery probe according to claim 1, further comprising:
e) a core of resilient material extending through said coil cautery electrode.

16. An electrocautery probe according to claim 15, wherein:
said core is made of one of nichrome, titanium, nickel-superalloy, cobalt-superalloy, and stainless steel.

17. An electrocautery probe having a variable morphology cautery electrode for performing cautery procedures, comprising:
a) a tubular member having a proximal end and a distal end;
b) at least one flexible cautery electrode capable of carrying a cautery current and extending at least partially out said distal end of said tubular member, said at least one electrode having a coil portion, a solid portion, and two ends, wherein at least one of said two ends is disposed within said tubular member;
c) adjustment means coupled to said tubular member and said at least one cautery electrode for moving one of (i) said at least one of said two ends, and (ii) said tubular member, relative to the other; and
d) a coupling means for coupling said at least one cautery electrode to a cautery voltage supply,
wherein said adjustment means for moving, when actuated, changes the morphology of said at least one cautery electrode.

18. An electrocautery probe kit, comprising:
a) a tubular member having a proximal end and a distal end;
b) a flexible coil electrode extending at least partially out of said distal end of said tubular member, said coil electrode having two ends;
c) an adjustment means coupled to said tubular member and said coil electrode for moving one of (i) said tubular member, and (ii) said at least one of said two ends, relative to the other;
d) a coupling means for coupling said coil electrode to a cautery voltage supply; and
e) a plurality of shape means selectively coupled to said tubular member and extending beyond said distal end of said tubular member, each shape means when coupled to said tubular member for imparting a different shape to said coil electrode,
wherein when said at least one of said two ends of said electrode is moved relative to one of said plurality of shape means, said coil electrode engages said one of said plurality of shape means which thereby changes a morphology of said coil electrode.

19. An electrocautery probe kit according to claim 18, wherein:
said plurality of shape means includes at least one slider extending through said tubular member, and a plurality of shaped heads, each of said plurality of shaped heads having means for coupling to said at least one slider.

20. An electrocautery probe kit according to claim 18, wherein:
said at least one slider consists of exactly one slider, and said means for coupling comprises means for removably coupling said shaped heads to said one slider.

* * * * *